(12) United States Patent
Kim

(10) Patent No.: US 11,759,353 B2
(45) Date of Patent: Sep. 19, 2023

(54) FROSTBITE PREVENTION PAD FOR CRYOLIPOLYSIS PROCEDURE

(71) Applicant: CLASSYS INC., Seoul (KR)

(72) Inventor: Dong Seok Kim, Seoul (KR)

(73) Assignee: CLASSYS INC., Seoul (KR)

( * ) Notice: Subject to any disclaimer, the term of this patent is extended or adjusted under 35 U.S.C. 154(b) by 706 days.

(21) Appl. No.: 16/645,256

(22) PCT Filed: Sep. 10, 2018

(86) PCT No.: PCT/KR2018/010548
§ 371 (c)(1),
(2) Date: Mar. 6, 2020

(87) PCT Pub. No.: WO2019/054706
PCT Pub. Date: Mar. 21, 2019

(65) Prior Publication Data
US 2020/0214881 A1 Jul. 9, 2020

(30) Foreign Application Priority Data
Sep. 12, 2017 (KR) .................. 10-2017-0116512

(51) Int. Cl.
*A61F 7/02* (2006.01)
*A61B 90/90* (2016.01)
*A61B 18/02* (2006.01)

(52) U.S. Cl.
CPC ............. *A61F 7/02* (2013.01); *A61B 18/02* (2013.01); *A61B 90/90* (2016.02); *A61F 2007/0288* (2013.01)

(58) Field of Classification Search
CPC ........................ A61F 7/02; A61F 2007/0288
See application file for complete search history.

(56) References Cited

U.S. PATENT DOCUMENTS

2015/0216816 A1    8/2015    O'Neil et al.

FOREIGN PATENT DOCUMENTS

| CN | 1210145 C | * | 7/2005 | ......... A41D 13/1209 |
|---|---|---|---|---|
| CN | 103405311 A | | 11/2013 | |
| CN | 104758123 A | | 7/2015 | |
| KR | 10-2007-0018490 A | | 2/2007 | |
| KR | 10-1292917 B1 | | 8/2013 | |
| KR | 20-2016-0001063 U | | 3/2016 | |

(Continued)

OTHER PUBLICATIONS

Machine Translation of CN1210145 C (Year: 2005).*
International Search Report for PCT/KR2018/010548 dated Dec. 20, 2018 from Korean Intellectual Property Office.

*Primary Examiner* — Kaitlyn E Smith
(74) *Attorney, Agent, or Firm* — Paratus Law Group, PLLC

(57) ABSTRACT

Disclosed is a frostbite prevention pad for a cryolipolysis procedure, which is used for a cryolipolysis procedure using a cryolipolysis device. The frostbite prevention pad includes: a base member made of a fiber material; one or more waterproof members made of a resin material and placed to overlap the base member; and one or more sewn parts formed by sewing the base member and the waterproof member to couple the base member and the waterproof member in a state in which the base member and the waterproof member overlap each other.

17 Claims, 7 Drawing Sheets

(56) References Cited

FOREIGN PATENT DOCUMENTS

| | | |
|---|---|---|
| KR | 10-2016-0080294 A | 7/2016 |
| KR | 10-1641162 B1 | 7/2016 |
| KR | 10-1693763 B1 | 1/2017 |
| RU | 2 576 830 C2 | 3/2016 |

* cited by examiner

FROSTBITE PREVENTION PAD FOR CRYOLIPOLYSIS PROCEDURE

CROSS-REFERENCE TO PRIOR APPLICATIONS

This application is a National Stage patent application of PCT International Patent Application No. PCT/KR2018/010548 (filed on Sep. 10, 2018) under 35 U.S.C. § 371, which claims priority to Korean Patent Application No. 10-2017-0116512 (filed on Sep. 12, 2017), which are all hereby incorporated by reference in their entirety.

BACKGROUND

The present invention relates to a frostbite prevention pad for a cryolipolysis procedure.

In general, a cryolipolysis procedure is one of the procedures for decomposing fat by a method other than exercise as the market associated with the diet increases. In the case of the cryolipolysis procedure, at a site where subcutaneous fat is to be reduced, the fat is sucked by a high air pressure, and then the fat below the epidermis is cooled and decomposed for about 1 hour by using a cooling plate having a temperature lowered to below zero degrees Celsius.

In this case, because the temperature of the cooling plate is about −9° C., not only the subcutaneous fat is cooled, but also the skin at the surgical site is cooled, which may cause adverse effects such as frostbite or necrosis. Therefore, the procedure is performed in a state in which a frostbite prevention pad containing a liquid-phase anti-freezing agent is attached to the surgical site.

However, when a hand piece of a cryolipolysis device is attached to a portion, where subcutaneous fat is to be reduced, and then negative pressure (vacuum) is generated, the anti-freezing agent contained in the frostbite prevention pad is sucked into the hand piece and drawn into a main body, which causes a breakdown of the cryolipolysis device.

In the related art, in order to solve the problem, a structure of a frostbite prevention pad disclosed in Korean Utility Model Application Laid-Open No. 20-2016-0001063 has a technical configuration including a first pad 210 onto which an anti-freezing gel is applied, and a film 230 joined to the first pad 210 in order to fix the anti-freezing gel applied onto the first pad 210, as illustrated in FIG. 1.

However, in the case of the structure of the frostbite prevention pad in the related art, there is a problem in that the film 230 is sucked into a hand piece (not illustrated) and the film 230 is torn during a process in which negative pressure is generated in the hand piece of the cryolipolysis device (not illustrated).

In addition, in the case of the structure of the frostbite prevention pad in the related art, a bonding agent is applied only onto a surface of the first pad 210, made of a non-woven fabric material, with which the film 230 comes into contact with, and as a result, there is a problem in that the first pad 210 is separated from the surface attached to the film 230 to another portion while the negative pressure is initially generated.

In addition, in the case of the structure of the frostbite prevention pad in the related art, the bonding agent needs to be applied onto the first pad 210 first before overlapping the first pad 210 and the film 230, and as a result, there is a problem in that the film 200 made of a thin vinyl material sways and changes in shape during the process of overlapping the first pad 210 and the film 230, and the film 200 is attached to the bonding agent at an undesired position, which makes the bonding process complicated and increases a product defect rate.

SUMMARY

A technical object of the present invention is to provide a frostbite prevention pad for a cryolipolysis procedure, in which a waterproof member may be prevented from being torn or the waterproof member and a base member may be prevented from being separated from each other during a process of generating negative pressure, and the waterproof member may be easily coupled to the base member without defects.

In order to achieve the above-mentioned object, a frostbite prevention pad for a cryolipolysis procedure according to an exemplary embodiment of the present invention is a frostbite prevention pad configured to be used for a cryolipolysis procedure using a cryolipolysis device, and the frostbite prevention pad includes a base member made of a fiber material; one or more waterproof members made of a resin material and placed to overlap the base member; and one or more sewn parts formed by sewing the base member and the waterproof member to couple the base member and the waterproof member in a state in which the base member and the waterproof member overlap each other.

The one or more sewn parts may include edge sewn parts formed by sewing edges of the waterproof member.

The edge sewn parts may include corner sewn lines formed by sewing four corners of the waterproof member.

As an example, the corner sewn line may have an inclined line shape, both ends of which are disposed at both sides based on the corner of the waterproof member.

As another example, the corner sewn line may have a Korean consonant "ㄴ" shape, both ends of which are disposed at both sides based on the corner of the waterproof member.

As still another example, the corner sewn line may have an arc shape, both ends of which are disposed at both sides based on the corner of the waterproof member.

As another example, the edge sewn parts may include long side sewn lines formed at two relatively long sides of the waterproof member and elongated in a longitudinal direction by a sewing process.

The one or more sewn parts may further include a center sewn part formed by sewing a central portion of the waterproof member.

As an example, the center sewn part may have a sewn line having a cross shape at the central portion of the waterproof member.

As another example, the center sewn part may have a quadrangular sewn line at the central portion of the waterproof member.

As still another example, the center sewn part may have a circular sewn line at the central portion of the waterproof member.

Each of the base member and the waterproof member may be stretchable in both a horizontal direction and a vertical direction.

The base member may have a greater elongation ratio than the waterproof member.

The base member may be impregnated with an anti-freezing agent.

A genuine product identification code may be formed on an outer surface of the waterproof member.

The genuine product identification code may be formed at a portion of the waterproof member where a hand piece of the cryolipolysis device is positioned, and the genuine product identification code may be detected by a detection unit provided on the hand piece.

The one or more waterproof members may include: a first waterproof member placed to overlap the base member and made of a resin material; and a second waterproof member placed to overlap the first waterproof member and made of a resin material, and the one or more sewn parts may be formed by sewing the base member, the first waterproof member, and the second waterproof member to combine the base member, the first waterproof member, and the second waterproof member in a state in which the base member, the first waterproof member, and the second waterproof member overlap one another.

A first vent hole may be formed in the first waterproof member, and a second vent hole may be formed in the second waterproof member so as not to overlap the first vent hole.

Position setting parts may be formed on the first and second waterproof members so that the first vent hole and the second vent hole do not overlap each other.

The position setting parts may include a first position identification line formed on the first waterproof member and disposed at one side based on a centerline of the first waterproof member; and a second position identification line formed on the second waterproof member and disposed at the other side based on the centerline of the first waterproof member, and the first and second vent holes may be prevented from overlapping each other when the first and second waterproof members overlap each other so that the first position identification line and the second position identification line are connected to each other.

The first and second position identification lines may be connected to each other and may define a portion where a hand piece of the cryolipolysis device is positioned.

The frostbite prevention pad for a cryolipolysis procedure according to the exemplary embodiment of the present invention configured as described above may have the following effects.

The exemplary embodiment of the present invention provides the technical configuration including a base member, one or more waterproof members, and one or more sewn parts, in which the one or more sewn parts are formed by sewing the base member and the waterproof member to couple the base member and the waterproof member in the state in which the base member and the waterproof member overlap each other. As a result, the long sewn line may be formed by the sewing process, such that unlike the related art, it is possible to prevent the waterproof member from being torn even though a load caused by negative pressure is concentrated on the portion of the waterproof member, where the sewn line is placed, during a process in which the negative pressure is generated in the hand piece of the cryolipolysis device.

According to the exemplary embodiment of the present invention, a hand-piece contact surface of the waterproof member and a skin contact surface of the base member are connected to each other by the sewing process. As a result, it is possible to prevent the problem in the related art that because the base member may also be sucked into the hand piece while the waterproof member is sucked into the hand piece by the negative pressure generated in the hand piece, the waterproof member and the base member are separated during the process of initially generating the negative pressure.

In addition, the exemplary embodiment of the present invention provides the technical configuration in which the sewing process is performed in the state in which the base member and the waterproof member overlap each other, and thus the position of the waterproof member does not deviate from the base member during the sewing process. As a result, unlike the related art, the waterproof member and the base member may be easily and accurately coupled, and thus it is possible to prevent a product defect that may be caused when the waterproof member and the base member are coupled at an undesired position.

DETAILED DESCRIPTION

Figure 1:
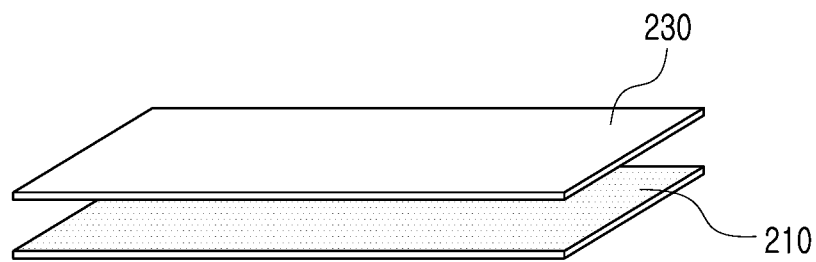
FIG. 1 is a view schematically illustrating a structure of a frostbite prevention pad in the related art.

Terms or words used in the specification and the claims should not be interpreted as being limited to a general or dictionary meaning and should be interpreted as a meaning and a concept which conform to the technical spirit of the present disclosure based on a principle that an inventor can appropriately define a concept of a term in order to describe his/her own invention by the best method.

Therefore, the exemplary embodiments disclosed in the present specification and the configurations illustrated in the drawings are just the best preferred exemplary embodiments of the present invention and do not represent all the technical spirit of the present invention. Accordingly, it should be appreciated that various equivalents and modified examples capable of substituting the exemplary embodiments may be made at the time of filing the present application.

Hereinafter, exemplary embodiments of the present disclosure will be described in detail with reference to the accompanying drawings so that those with ordinary skill in the art to which the present disclosure pertains may easily carry out the exemplary embodiments. However, the present invention may be implemented in various different ways and is not limited to the exemplary embodiments described herein.

Figure 2:
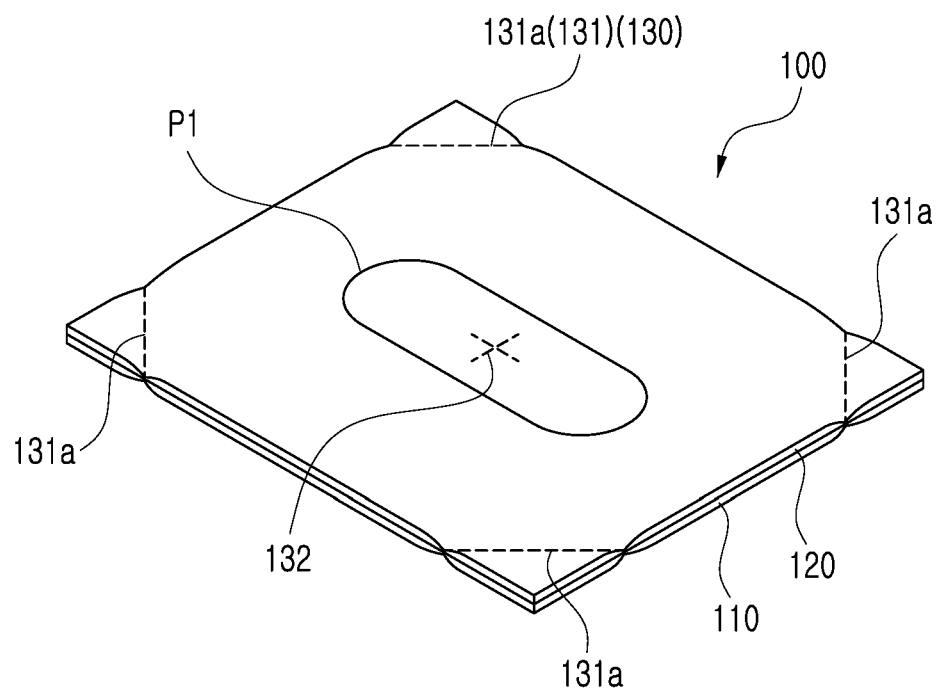
FIG. 2 is a perspective view schematically illustrating a frostbite prevention pad for a cryolipolysis procedure according to a first exemplary embodiment of the present invention.
Figure 3:
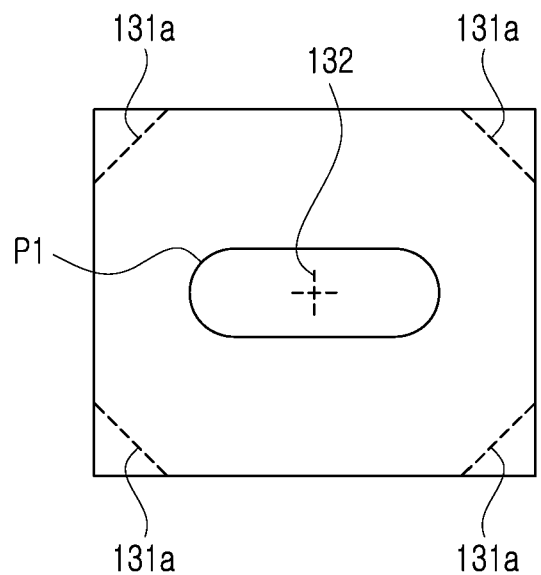
FIG. 3 is a view illustrating the frostbite prevention pad for a cryolipolysis procedure illustrated in FIG. 2 when viewed from above.

FIG. 2 is a perspective view schematically illustrating a frostbite prevention pad for a cryolipolysis procedure according to a first exemplary embodiment of the present invention, and FIG. 3 is a view illustrating the frostbite prevention pad for a cryolipolysis procedure illustrated in FIG. 2 when viewed from above.

Figure 4:
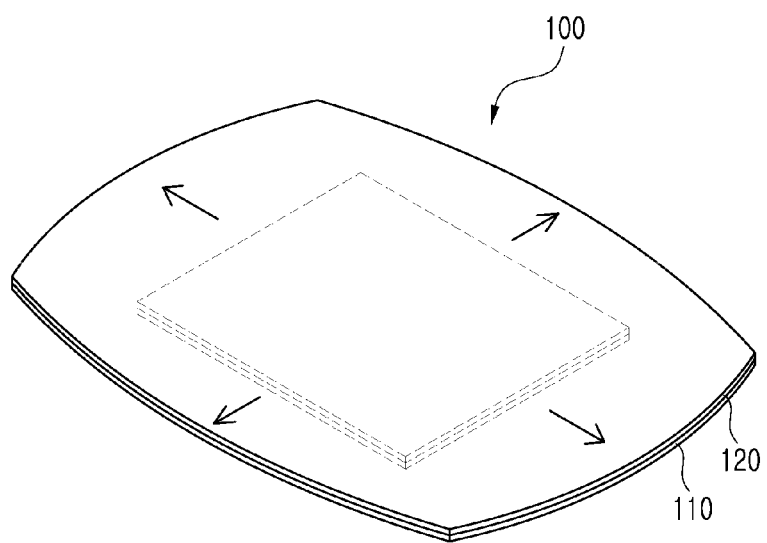
FIG. 4 is a view schematically illustrating a state in which the frostbite prevention pad for a cryolipolysis procedure illustrated in FIG. 2 is stretched.
Figure 5:
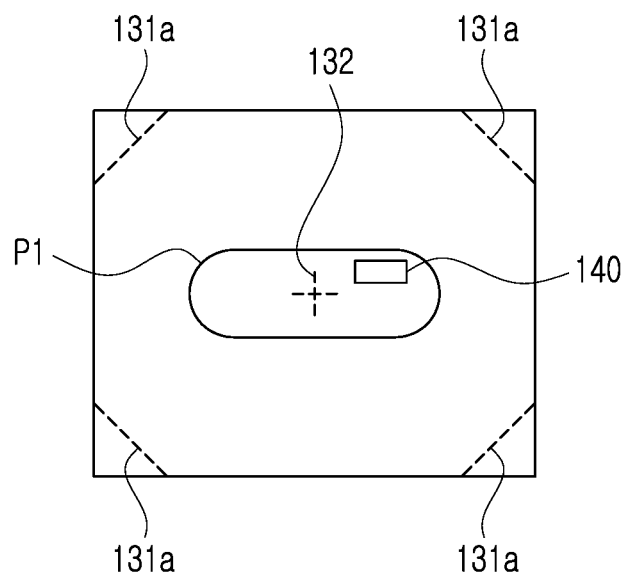
FIG. 5 is a view schematically illustrating a state in which a genuine product identification code is printed on the frostbite prevention pad for a cryolipolysis procedure illustrated in FIG. 2.

FIG. 4 is a view schematically illustrating a state in which the frostbite prevention pad for a cryolipolysis procedure illustrated in FIG. 2 is stretched, and FIG. 5 is a view schematically illustrating a state in which a genuine product identification code is printed on the frostbite prevention pad for a cryolipolysis procedure illustrated in FIG. 2.

A frostbite prevention pad 100 for a cryolipolysis procedure according to a first exemplary embodiment of the present invention is a frostbite prevention pad used for a cryolipolysis procedure using a cryolipolysis device (not illustrated) and includes a base member 110, a waterproof member 120, and one or more sewn parts 130, as illustrated in FIGS. 2 to 5. Hereinafter, the respective constituent elements will be described in detail with reference to FIGS. 2 to 5.

The base member 110 is a constituent element configured to come into direct contact with the skin at the treatment area, and the base member 110 may be made of a fiber material in the form of a non-woven fabric.

Therefore, an anti-freezing agent in a gel or liquid phase may be easily absorbed into the fiber material of the base member 110. The anti-freezing agent absorbed into the base member 110 remains on the skin during the cryolipolysis procedure, thereby preventing the surface of the skin from freezing at a temperature below zero degrees Celsius. Ultimately, when a cooling plate (e.g., a cooling unit of a thermoelectric module) (not illustrated) provided on a hand piece (not illustrated) of the cryolipolysis device (not illustrated) comes into contact with the skin, the base member 110 may prevent the frostbite of the skin and the subcutaneous fat may be cooled while the cold of the cooling plate is transferred to the subcutaneous fat.

Further, as illustrated in FIG. 4, the base member 110 may be made of a material that may be stretched in both a horizontal direction and a vertical direction. Therefore, the base member 110 may be smoothly stretched in all directions while the skin is sucked into the hand piece by negative pressure generated in the hand piece, such that it is possible to prevent the base member 110 from being torn.

For example, the base member 110 may be made of any one of a fiber assembly and a polymer compound sheet so that the base member 110 may be absorbent and stretched in both the horizontal direction and the vertical direction. Here, the fiber assembly may be made of any one or more of natural fibers, chemical fibers, woven fabrics, knitted fabrics, mesh, short fibers, long fibers, and non-woven fabrics. Further, the base member 110 may have a greater elongation than the waterproof member 120.

The waterproof member 120 is a constituent element that prevents the anti-freezing agent absorbed into the base member 110 from being drawn into the cryolipolysis device (not illustrated) through the hand piece (not illustrated). The waterproof member 120 may be made of a resin material in the form of a waterproof fabric and may have no vent hole. As illustrated in FIG. 2, the waterproof member 120 may overlap the base member 110.

Further, as illustrated in FIG. 4, the waterproof member 120 may be made of a material that may be stretched in both the horizontal direction and the vertical direction. Therefore, the waterproof member 120, together with the base member 110, may also be smoothly stretched in all directions while the skin is sucked into the hand piece by the negative pressure generated in the hand piece, such that it is possible to prevent the waterproof member 120 from being torn. If the waterproof member 120 is torn, the anti-freezing agent is drawn into the cryolipolysis device by the hand piece through the torn portion, which may cause a breakdown of the device.

For example, the base member 110 may be made of any one or more of polyurethane, polyethylene (PE), polypropylene (PP), polyester, polyether ester, polyolefin, polyether, polyethylene terephthalate (PET), polybutylene terephthalate (PBT), polytrimethylene terephthalate (PTT), silicone resin, ethylene-vinyl acetate copolymer (EVA), and polymer synthetic resin so that the base member 110 may be waterproof and stretched in both the horizontal direction and the vertical direction.

The one or more sewn parts 130 are constituent elements that couple the base member 110 and the waterproof member 120 in the state in which the base member 110 and the waterproof member 120 overlap each other. The one or more sewn parts 130 may be formed by sewing the base member 110 and the waterproof member 120 by using a sewing machine or the like.

Therefore, since there may be long sewn lines formed through the sewing process, it is possible to prevent the waterproof member 120 from being torn, unlike the related art, even though a load caused by the negative pressure is concentrated on the portions of the waterproof member 120, where the sewn lines are placed, during the process of generating the negative pressure in the hand piece (not illustrated) of the cryolipolysis device (not illustrated). In addition, a hand-piece contact surface (an outer surface of the waterproof member with which the hand piece comes into contact) of the waterproof member 120 is connected to a skin contact surface (a surface of the base member with which the skin comes into contact) of the base member 110 by the sewing process. Therefore, it is possible to prevent the problem in the related art that because the base member 110 may also be sucked into the hand piece while the waterproof member 120 is sucked into the hand piece by the negative pressure generated in the hand piece, the waterproof member 120 and the base member 110 are separated during the process of initially generating the negative pressure. In addition, the present invention provides the technical configuration in which the sewing process is performed in the state in which the base member 110 and the waterproof member 120 overlap each other, and thus the position of the waterproof member 120 does not deviate from the base member 110 during the sewing process. Therefore, unlike the related art, the waterproof member 120 and the base member 110 may be easily and accurately coupled, and thus it is possible to prevent a product defect that may be caused when the waterproof member 120 and the base member 110 are coupled at an undesired position.

As illustrated in FIGS. 2 and 3, the one or more sewn parts 130 may include edge sewn parts 131 and a center sewn part 132. The edge sewn parts 131 may be formed by sewing edges of the waterproof member 120, and the center sewn part 132 may be formed by sewing a central portion of the waterproof member 120. In particular, the center sewn part 132 serves to fix the position of the central portion of the waterproof member 120 to the base member 110 and also to hold the waterproof member 120 and the base member 110 together so that the waterproof member 120 and the base member 110 are simultaneously sucked into the hand piece when the negative pressure is generated in the hand piece.

For example, as illustrated in FIGS. 2 and 3, the edge sewn parts 131 may be corner sewn lines 131a by sewing four corners of the waterproof member 120. In particular, the corner sewn line 131a may have an inclined line shape, both ends of which are disposed at both sides based on the corner of the waterproof member 120. That is, the corner sewn line 131a may define a triangular shape together with outer periphery lines of the corner portion of the waterproof member 120. Therefore, since the sewn line is implemented in the form of the inclined straight line, the corner sewn line 131a may be easily and quickly formed.

Further, as illustrated in FIGS. 2 and 3, the center sewn part 132 may have a sewn line having a cross shape and formed at the central portion of the waterproof member 120. Therefore, the sewn line is implemented in the form of cross straight lines, the center sewn line may be easily and quickly formed.

Furthermore, as illustrated in FIG. 5, a genuine product identification code 140 may be formed on an outer surface of the waterproof member 120. For example, a bar code, a QR code, a serial number, or the like may be used as the genuine product identification code 140.

As illustrated in FIG. 5, the genuine product identification code 140 may be formed within a boundary line of a portion P1 of the waterproof member 120 where the hand piece is positioned. Therefore, in a case in which a detection unit (not illustrated) such as a scanner is mounted on the hand piece and the cryolipolysis device is provided with a controller (not illustrated), the controller determines whether the frostbite prevention pad is the genuine product based on the genuine product identification code 140 detected by the detection unit, and the controller may allow the cryolipolysis device to operate only when the frostbite prevention pad is the genuine product.

Hereinafter, a frostbite prevention pad 200 for a cryolipolysis procedure according to a second exemplary embodiment of the present invention will be described with reference to FIG. 6.

Figure 6:
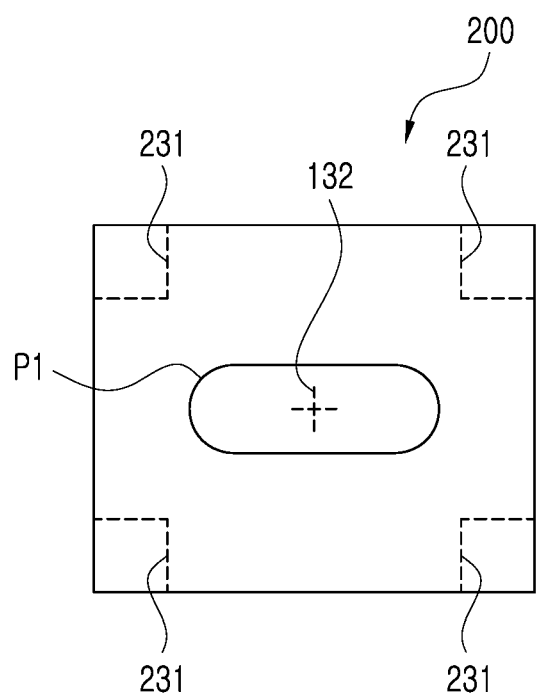
FIG. 6 is a view schematically illustrating a frostbite prevention pad for a cryolipolysis procedure according to a second exemplary embodiment of the present invention.

FIG. 6 is a view schematically illustrating the frostbite prevention pad for a cryolipolysis procedure according to the second exemplary embodiment of the present invention.

As illustrated in FIG. 6, because the frostbite prevention pad 200 for a cryolipolysis procedure according to the second exemplary embodiment of the present invention is identical to the above-mentioned frostbite prevention pad according to the first exemplary embodiment of the present invention except for shapes of corner sewn lines 231, the description will be made below by focusing on the shape of the corner sewn line 231.

The corner sewn line 231 may have a Korean consonant " ㄴ " shape, both ends of which are disposed at both sides based on the corner of the waterproof member 120. That is, the corner sewn line 231 may define a quadrangular shape together with outer periphery lines of the corner portion of the waterproof member 120. Therefore, when the corner sewn line 231 is unfolded, the corner sewn line 231 has a longer length than the corner sewn line 131a having the inclined line shape according to the first exemplary embodiment of the present invention, such that it is possible to further improve coupling force.

Hereinafter, a frostbite prevention pad 300 for a cryolipolysis procedure according to a third exemplary embodiment of the present invention will be described with reference to FIG. 7.

Figure 7:
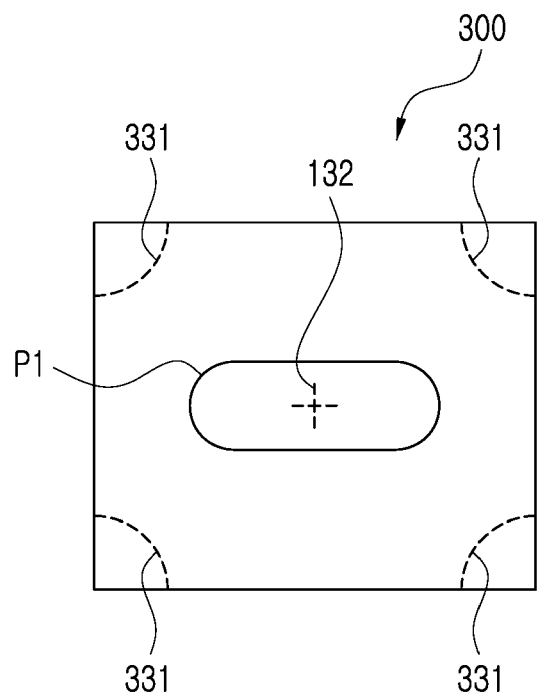
FIG. 7 is a view schematically illustrating a frostbite prevention pad for a cryolipolysis procedure according to a third exemplary embodiment of the present invention.

FIG. 7 is a view schematically illustrating the frostbite prevention pad for a cryolipolysis procedure according to the third exemplary embodiment of the present invention.

As illustrated in FIG. 7, because the frostbite prevention pad 300 for a cryolipolysis procedure according to the third exemplary embodiment of the present invention is identical to the above-mentioned frostbite prevention pad according to the first exemplary embodiment of the present invention except for shapes of corner sewn lines 331, the description will be made below by focusing on the shape of the corner sewn line 331.

The corner sewn line 331 may have an arc shape, both ends of which are disposed at both sides based on the corner of the waterproof member 120. That is, the corner sewn line 331 may define a quadrant shape together with outer periphery lines of the corner portion of the waterproof member 120. Therefore, when the corner sewn line 331 is unfolded, the corner sewn line 331 has a longer length than the corner sewn line 131a having the inclined line shape according to the first exemplary embodiment of the present invention, such that it is possible to further improve coupling force. Unlike the above-mentioned corner sewn line 231 having the " ㄴ " shape according to the second exemplary embodiment of the present invention, there is no portion (notch portion) sharply bent at approximately 90 degrees. Therefore, it is possible to effectively support a load to be applied to the corner sewn line 331.

Hereinafter, a frostbite prevention pad 400 for a cryolipolysis procedure according to a fourth exemplary embodiment of the present invention will be described with reference to FIG. 8.

Figure 8:
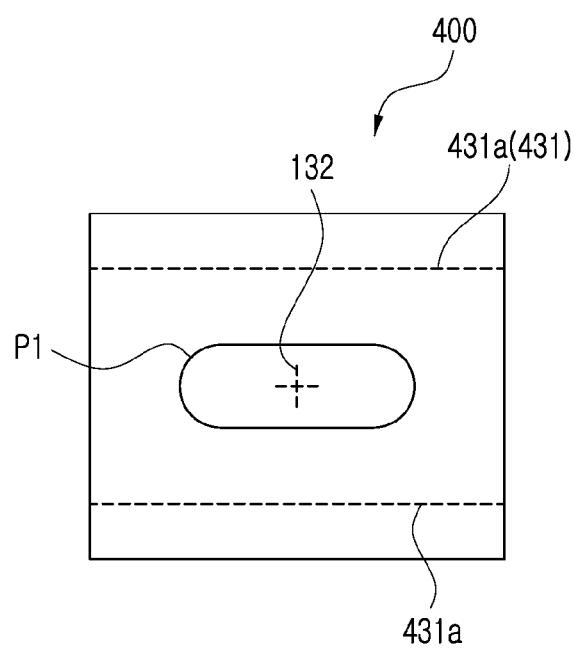
FIG. 8 is a view schematically illustrating a frostbite prevention pad for a cryolipolysis procedure according to a fourth exemplary embodiment of the present invention.

FIG. 8 is a view schematically illustrating the frostbite prevention pad for a cryolipolysis procedure according to the fourth exemplary embodiment of the present invention.

As illustrated in FIG. 8, because the frostbite prevention pad 400 for a cryolipolysis procedure according to the fourth exemplary embodiment of the present invention is identical to the above-mentioned frostbite prevention pad according to the first exemplary embodiment of the present invention except for positions and shapes of edge sewn parts 431, the description will be made below by focusing on the position and the shape of the edge sewn part 431.

The edge sewn parts 431 may be long side sewn lines 431a formed at two relatively long sides of the waterproof member 120 and elongated in a longitudinal direction by a sewing process. Therefore, in comparison with the above-mentioned four corner sewn lines 131a according to the first exemplary embodiment of the present invention, the number of sewn lines is reduced to two, such that the long side sewn lines 431a may be easily and quickly formed. In addition, the long side sewn line 431a has a much longer length than the corner sewn line 131a having the above-mentioned inclined line shape according to the first exemplary embodiment of the present invention, such that it is possible to further improve coupling force.

Hereinafter, a frostbite prevention pad 500 for a cryolipolysis procedure according to a fifth exemplary embodiment of the present invention will be described with reference to FIG. 9.

Figure 9:
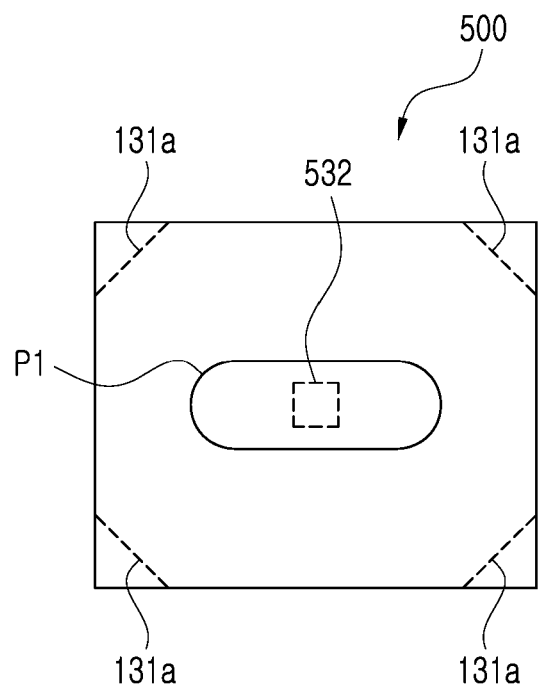
FIG. 9 is a view schematically illustrating a frostbite prevention pad for a cryolipolysis procedure according to a fifth exemplary embodiment of the present invention.

FIG. 9 is a view schematically illustrating the frostbite prevention pad for a cryolipolysis procedure according to the fifth exemplary embodiment of the present invention.

As illustrated in FIG. 9, because the frostbite prevention pad 500 for a cryolipolysis procedure according to the fifth exemplary embodiment of the present invention is identical to the above-mentioned frostbite prevention pad according to the first exemplary embodiment of the present invention except for shapes of center sewn parts 532, the description will be made below by focusing on the shape of the center sewn part 532.

The center sewn part 532 may have a quadrangular sewn line formed at the central portion of the waterproof member 120. Therefore, when the sewn line 532 is unfolded, the sewn line 532 has a longer overall length than the above-mentioned sewn line 132 having the cross shape according to the first exemplary embodiment of the present invention, such that it is possible to further improve coupling force.

Hereinafter, a frostbite prevention pad 600 for a cryolipolysis procedure according to a sixth exemplary embodiment of the present invention will be described with reference to FIG. 10.

Figure 10:
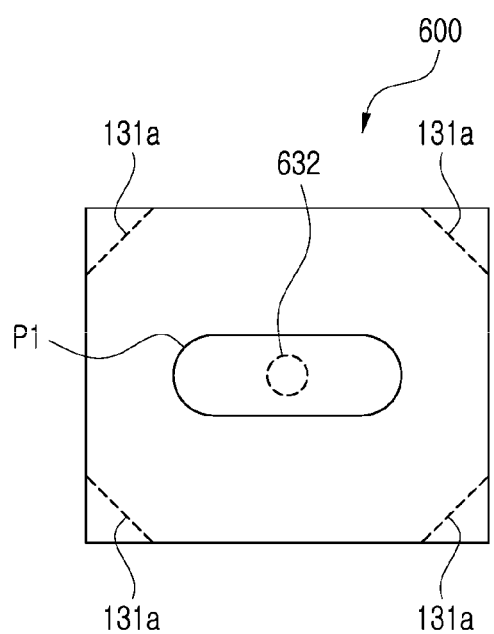
FIG. 10 is a view schematically illustrating a frostbite prevention pad for a cryolipolysis procedure according to a sixth exemplary embodiment of the present invention.

FIG. 10 is a view schematically illustrating the frostbite prevention pad for a cryolipolysis procedure according to the sixth exemplary embodiment of the present invention.

As illustrated in FIG. 10, because the frostbite prevention pad 600 for a cryolipolysis procedure according to the sixth exemplary embodiment of the present invention is identical to the above-mentioned frostbite prevention pad according to the first exemplary embodiment of the present invention except for shapes of center sewn parts 632, the description will be made below by focusing on the shape of the center sewn part 632.

The center sewn part 632 may have a circular sewn line formed at the central portion of the waterproof member 120. Therefore, when the sewn line 632 is unfolded, the sewn line 632 has a longer overall length than the above-mentioned sewn line 132 having the cross shape according to the first exemplary embodiment of the present invention, such that it is possible to further improve coupling force. Unlike the above-mentioned quadrangular sewn line 532 according to the fifth exemplary embodiment of the present invention, there is no portion (notch portion) sharply bent at approximately 90 degrees. Therefore, it is possible to effectively support a load to be applied to the sewn line.

Hereinafter, a frostbite prevention pad 700 for a cryolipolysis procedure according to a seventh exemplary embodiment of the present invention will be described with reference to FIGS. 11 and 12.

Figure 11:
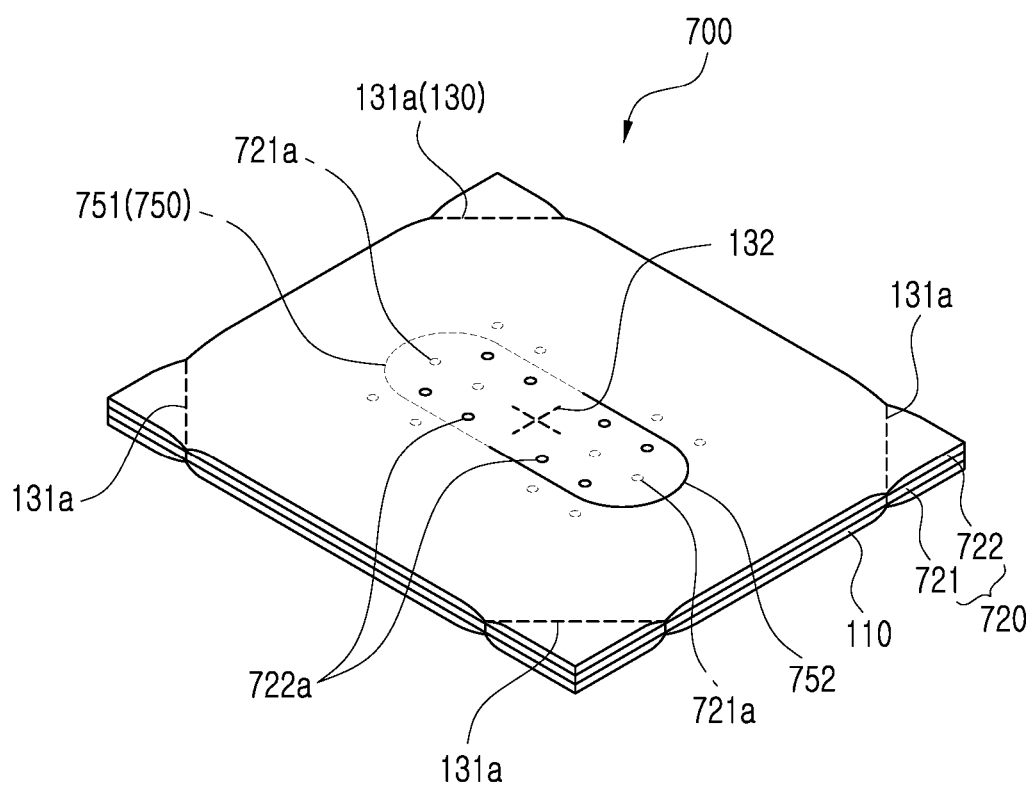
FIG. 11 is a perspective view schematically illustrating a frostbite prevention pad for a cryolipolysis procedure according to a seventh exemplary embodiment of the present invention.
Figure 12:
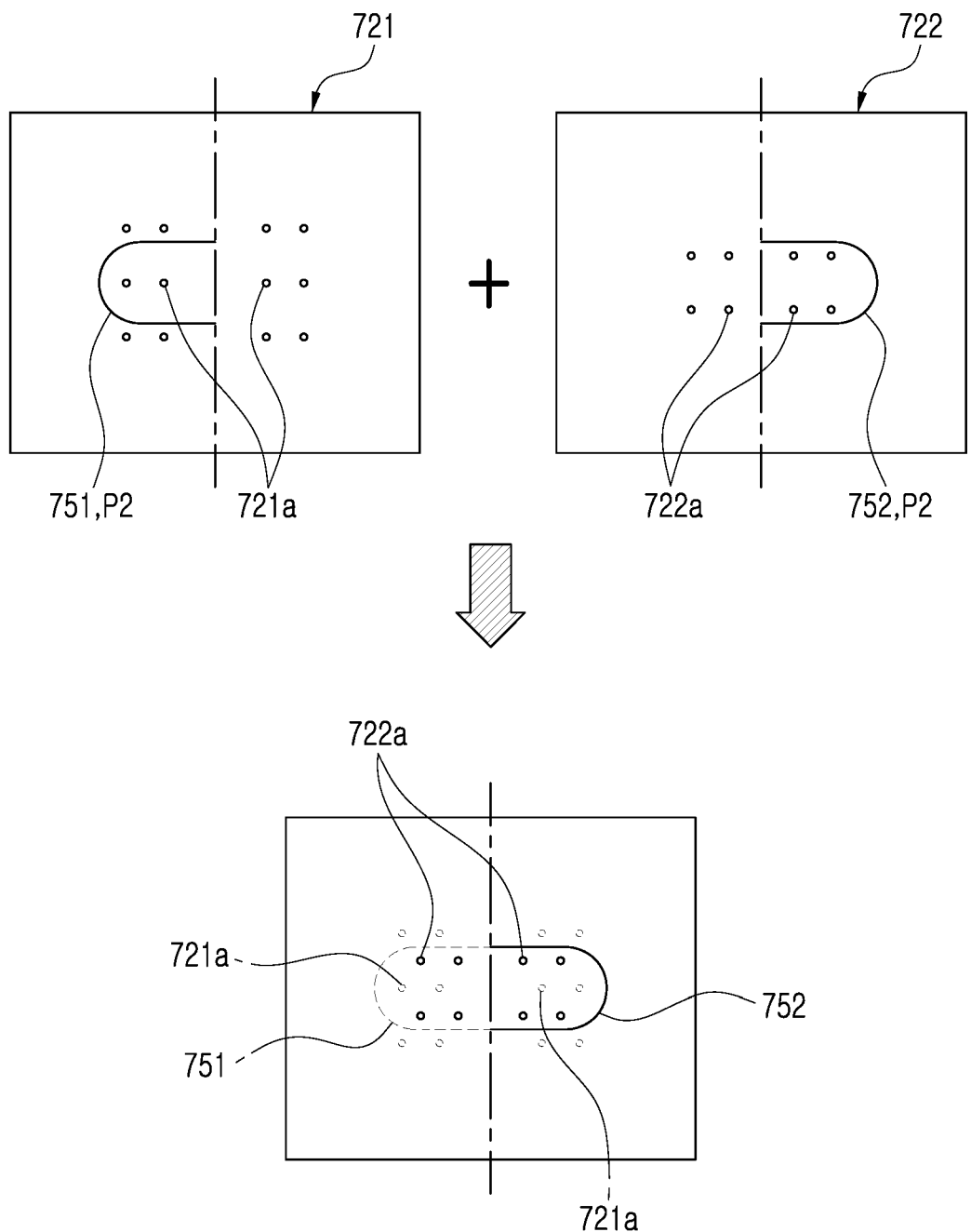
FIG. 12 is a view schematically illustrating a process in which first and second waterproof pads of the frostbite prevention pad for a cryolipolysis procedure illustrated in FIG. 11 overlap each other.

FIG. 11 is a perspective view schematically illustrating the frostbite prevention pad for a cryolipolysis procedure according to the seventh exemplary embodiment of the present invention, and FIG. 12 is a view schematically illustrating a process in which first and second waterproof pads of the frostbite prevention pad for a cryolipolysis procedure illustrated in FIG. 11 overlap each other.

As illustrated in FIGS. 11 and 12, because the frostbite prevention pad 700 for a cryolipolysis procedure according to the seventh exemplary embodiment of the present invention is identical to the above-mentioned frostbite prevention pad according to the first exemplary embodiment of the present invention except that one or more waterproof members 720 include first and second waterproof members 721 and 722, the description will be made below by focusing on this configuration.

As illustrated in FIGS. 11 and 12, the one or more waterproof members 720 may include the first and second waterproof members 721 and 722. The first waterproof member 721 may be placed to overlap the base member 110 and made of a waterproof and stretchable resin material, and the second waterproof member 722 may be placed to overlap the first waterproof member 721 and made of a waterproof and stretchable resin material identical to the material of the first waterproof member 721. For example, the first and second waterproof members 721 and 722 may be made of a material identical to the material of the above-mentioned waterproof member 120 according to the first exemplary embodiment of the present invention.

As illustrated in FIG. 11, the one or more sewn parts 130 may be formed by sewing the base member 110, the first waterproof member 721, and the second waterproof member 722 to combine the base member 110, the first waterproof member 721, and the second waterproof member 722 in a state in which the base member 110, the first waterproof member 721, and the second waterproof member 722 overlap one another.

Further, as illustrated in FIG. 12, first vent holes 721a may be formed in the first waterproof member 721, and second vent holes 722a may be formed in the second waterproof member 722. Here, the first and second vent holes 721a and 722a may serve as passageways through which the negative pressure generated in the hand piece (not illustrated) is transmitted to the skin. In addition, the first and second vent holes 721a and 722a may be disposed so as not to overlap one another so that the anti-freezing agent absorbed into the base member 110 is not drawn into the hand piece (not illustrated) through the first and second vent holes 721a and 722a.

In particular, as illustrated in FIG. 12, position setting parts 750 may be formed on the first and second waterproof members 721 and 722 so that the first vent hole 721a and the second vent hole 722a do not overlap each other. For example, as illustrated in FIG. 12, the position setting parts 750 may include a first position identification line 751 formed on the first waterproof member 721 and disposed at one side based on a centerline of the first waterproof member 721, and a second position identification line 752 formed on the second waterproof member 722 and disposed at the other side based on the centerline of the first waterproof member 721. Therefore, the first and second vent holes 721a and 722a may be prevented from overlapping one another when the first and second waterproof members 721 and 722 overlap each other to connect the first position identification line 751 and the second position identification line 752.

Furthermore, when the first and second position identification lines 751 and 752 are connected to each other, the first and second position identification lines 751 and 752 may also define a portion P2 where the hand piece (not illustrated) of the cryolipolysis device is positioned.

The foregoing detailed description illustrates the present invention. Further, the foregoing description merely shows and describes the exemplary embodiments of the present invention, and the present invention can be used in various other combinations, modifications, and environments. That is, alterations or modifications may be made within the scope of the concept of the invention disclosed in the present specification, the scope equivalent to the described disclosure, and/or the scope of the technology or knowledge in the art. The above-mentioned exemplary embodiments are provided to explain the best state in carrying out the present invention, other inventions associated with the present invention may be practiced in other ways known in the art, and various modifications required for the specific fields of application and the use of the present invention may be made. Thus, the detailed description of the present invention is not intended to limit the present invention to the disclosed exemplary embodiments. Moreover, the appended claims should be construed to include other exemplary embodiments.

Various aspects for carrying out the present invention have been described in the best mode for carrying out the invention.

The present invention relates to a pad for preventing frostbite during a cryolipolysis procedure and is applicable to a cryolipolysis device.

The invention claimed is:

1. A frostbite prevention pad for a cryolipolysis procedure, which is used for a cryolipolysis procedure using a cryolipolysis device, the frostbite prevention pad comprising:
a base member made of a fiber material;
one or more waterproof members made of a resin material and placed to overlap the base member; and
one or more sewn parts which fix the base member and the one or more waterproof members together to couple the base member and the one or more waterproof members in a state in which the base member and the one or more waterproof members overlap each other,
wherein the one or more sewn parts comprise edge sewn parts which fix the one or more waterproof members and the base member together at edges of the frostbite prevention pad and a center sewn part which fix the one or more waterproof members and the base member together at a central portion of the frostbite prevention pad such that the one or more waterproof members is prevented from being torn or being separated from the base member while a negative pressure is generated by the cryolipolysis device,
wherein the one or more waterproof members comprise:
a first waterproof member placed to overlap the base member and made of a resin material; and
a second waterproof member placed to overlap the first waterproof member and made of a resin material,
wherein the one or more sewn parts fix the base member, the first waterproof member, and the second waterproof member together to combine the base member, the first waterproof member, and the second waterproof member in a state in which the base member, the first waterproof member, and the second waterproof member overlap one another, and
wherein a first vent hole is formed in the first waterproof member, and a second vent hole is formed in the second waterproof member so as not to overlap the first vent hole.

2. The frostbite prevention pad of claim 1, wherein the edge sewn parts comprise corner sewn lines formed at four corners of the one or more waterproof members.

3. The frostbite prevention pad of claim 2, wherein each corner sewn line has an inclined line shape, and both ends of each corner sewn line are disposed at sides the corner of frostbite prevention pad.

4. The frostbite prevention pad of claim 2, wherein each corner sewn line has a Korean consonant "ㄴ" shape, and both ends of each corner sewn line are disposed at sides the corner of the frostbite prevention pad.

5. The frostbite prevention pad of claim 2, wherein each corner sewn line has an arc shape, and both ends of each corner sewn line are disposed at sides the corner of the frostbite prevention pad.

6. The frostbite prevention pad of claim 1, wherein the edge sewn parts comprise long side sewn lines formed at two relatively long sides of the frostbite prevention pad and elongated in a longitudinal direction of the frostbite prevention pad.

7. The frostbite prevention pad of claim 1, wherein the center sewn part has a sewn line having a cross shape at the central portion of the frostbite prevention pad.

8. The frostbite prevention pad of claim 1, wherein the center sewn part has a quadrangular sewn line at the central portion of the frostbite prevention pad.

9. The frostbite prevention pad of claim 1, wherein the center sewn part has a circular sewn line at the central portion of the frostbite prevention pad.

10. The frostbite prevention pad of claim 1, wherein each of the base member and the one or more waterproof members is stretchable in both a horizontal direction and a vertical direction.

11. The frostbite prevention pad of claim 10, wherein the base member has a greater elongation ratio than the one or more waterproof members.

12. The frostbite prevention pad of claim 1, wherein the base member is impregnated with an anti-freezing agent.

13. The frostbite prevention pad of claim 1, wherein a genuine product identification code is formed on an outer surface of the one or more waterproof members.

14. The frostbite prevention pad of claim 13, wherein the genuine product identification code is formed at a portion of the one or more waterproof members where a hand piece of the cryolipolysis device is positioned, and the genuine product identification code is detected by a detection unit provided on the hand piece.

15. The frostbite prevention pad of claim 1, wherein position setting parts are formed on the first and second waterproof members so that the first vent hole and the second vent hole do not overlap each other.

16. The frostbite prevention pad of claim 15, wherein the position setting parts comprise:
a first position identification line formed on the first waterproof member and disposed at one side based on a centerline of the first waterproof member; and
a second position identification line formed on the second waterproof member and disposed at the other side based on the centerline of the first waterproof member, and
the first and second vent holes are prevented from overlapping each other when the first and second waterproof members overlap each other so that the first position identification line and the second position identification line are connected to each other.

17. The frostbite prevention pad of claim 16, wherein the first and second position identification lines are connected to each other and define a portion where a hand piece of the cryolipolysis device is positioned.

* * * * *